(12) United States Patent
Hoelz et al.

(10) Patent No.: US 7,932,023 B2
(45) Date of Patent: Apr. 26, 2011

(54) CSPCNA ISOFORM MODIFICATIONS AND USES THEREOF

(75) Inventors: Derek J. Hoelz, Indianapolis, IN (US); Robert J. Hickey, Indianapolis, IN (US); Linda H. Malkas, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 309 days.

(21) Appl. No.: 11/993,252

(22) PCT Filed: Jun. 26, 2006

(86) PCT No.: PCT/US2006/024774
§ 371 (c)(1),
(2), (4) Date: Feb. 15, 2008

(87) PCT Pub. No.: WO2007/002574
PCT Pub. Date: Jan. 4, 2007

(65) Prior Publication Data
US 2009/0061432 A1    Mar. 5, 2009

Related U.S. Application Data

(60) Provisional application No. 60/694,159, filed on Jun. 27, 2005.

(51) Int. Cl.
*C12Q 1/00*    (2006.01)

(52) U.S. Cl. .......................................... 435/4
(58) Field of Classification Search .................. None
See application file for complete search history.

(56) References Cited

U.S. PATENT DOCUMENTS

2003/0162233 A1    8/2003    Malkas et al.

OTHER PUBLICATIONS

Bechtel et al (Cancer Research, 1998, 58:3264-3269).*
Hoelz et al, Proteomics, 2006, 6:4808-4816, IDS.*
Bechtel et al., "A unique form of proliferating cell nuclear antigen is present in malignant breast cells," *Cancer Res., Amer. Assoc. for Cancer Res.*, 58: 3264-3269 (1998).
Hoelz et al., "The discovery of labile methyl esters on proliferating cell nuclear antigen by MS/MS." *Proteomics*, 6(17): 4808-4816 (2006).
Malkas et al., "A cancer-specific form of proliferating cell nuclear antigen (csPCNA) is present in malignant human breast cells and tissues," *Jrnl of Clin. Ligand Assay*, 25(1): 20-32 (2002).
Naryzhny et al., "Observation of multiple isoforms and specific proteolysis patterns of proliferating cell nuclear antigen in the context of cell cycle compartments and sample preparations," *Proteomics*, 3(6): 930-936 (2003).

* cited by examiner

*Primary Examiner* — Laura B Goddard
(74) *Attorney, Agent, or Firm* — Barnes & Thornburg LLP

(57) ABSTRACT

Methods and compositions to detect the presence of csPCNA isoform by identifying one or more posttranslational modifications are disclosed. Methods to identify csPCNA isoform through posttranslational modifications including methylesterification levels are disclosed.

9 Claims, 10 Drawing Sheets

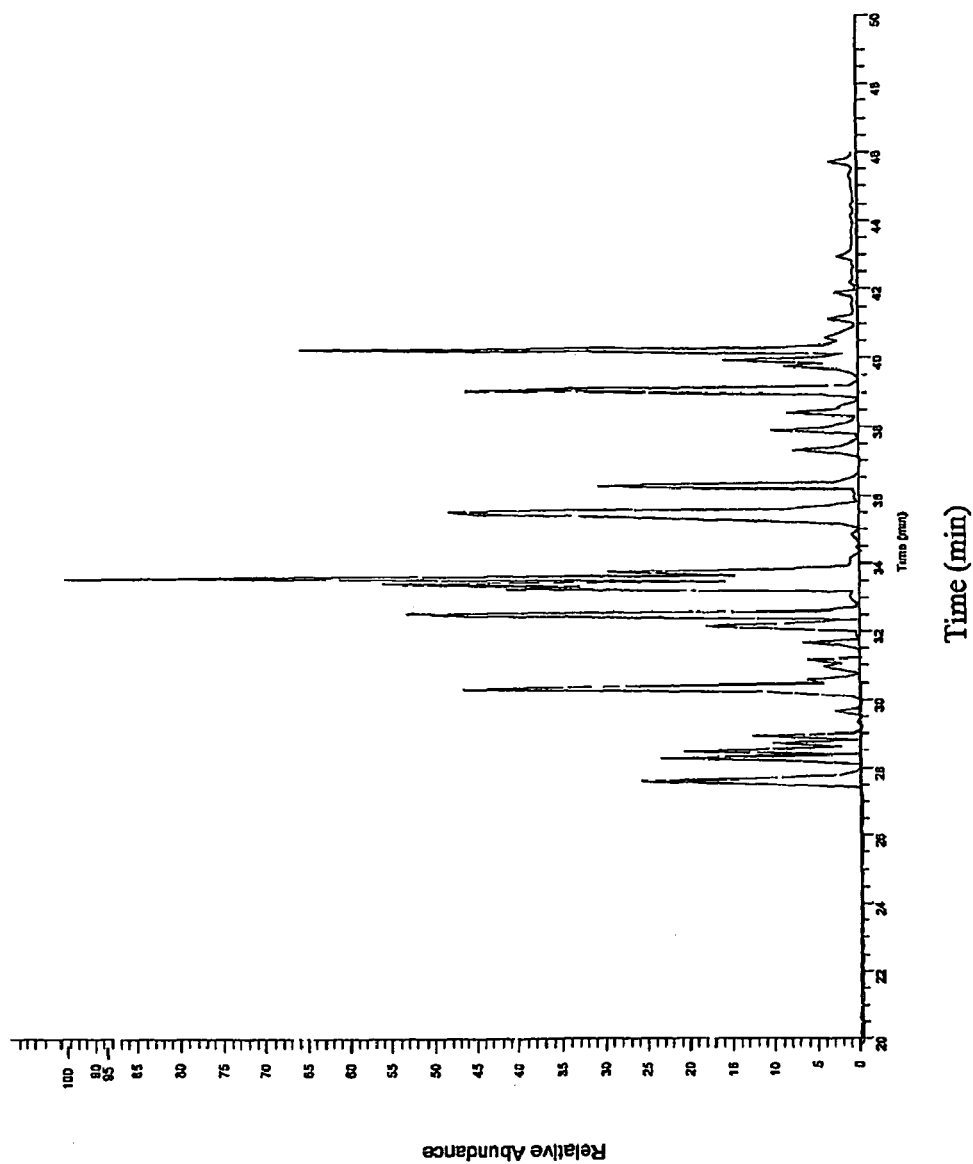
FIG. 1A-B

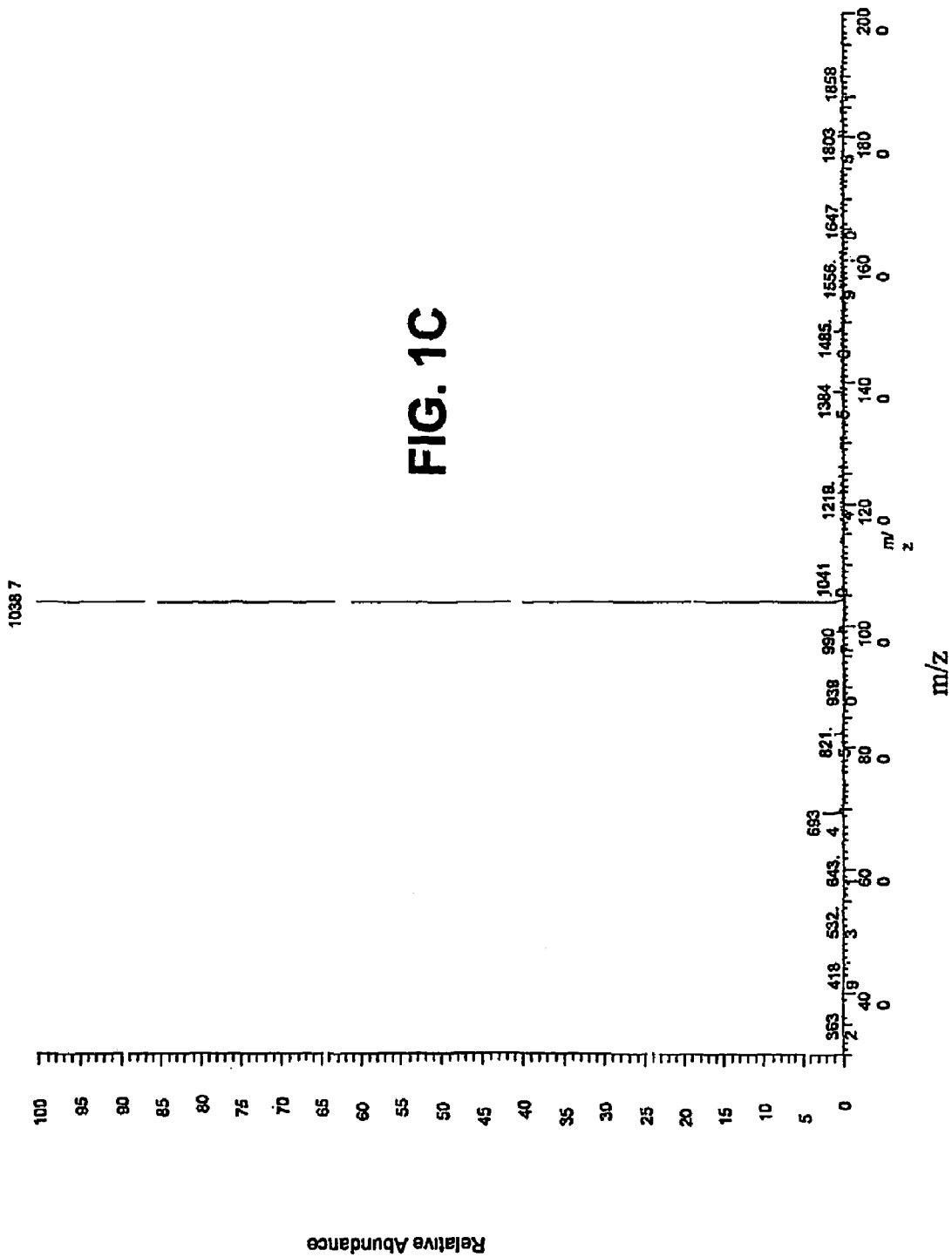

B

|  | 10 | 20 | 30 | 40 | 50 |
|---|---|---|---|---|---|
| Trypsin: | MFE<sub>m</sub>ARLVQGS | ILKKVLEALK | DLINEACWDI | SSSGVNLQSM | DSSHVSLVQL |
| Tryp/CNBr: | MFE<sub>m</sub>ARLVQGS | ILKKVLEALK | DLINEACWDI | SSSGVNLQSM | DSSHVSLVQL |
| GluC: |  | ALK | DLINEACWDI | SSSGVNLQSM | DSSHVSLVQL |
| AspN: |  |  | DLINEACWDI | SSSGVNLQSM | DSSHVSLVQL |

|  | 60 | 70 | 80 | 90 | 100 |
|---|---|---|---|---|---|
|  | TLRSEGFDTY | RCDRNLAMGV | NLTSMSKILK | CAGNE<sub>m</sub>DIITL | RAE<sub>m</sub>D<sub>m</sub>NADTLA |
|  | TLRSEGFDTY | RCDRNLAMGV | NLTSMSKILK | CAGNE<sub>m</sub>DIITL | RAEDNADTLA |
|  | TLRSE |  |  |  |  |
|  | TLRSEGF | DRNLAMGV | NLTSMSKILK | CAGNEDIITL | RAEDNADTLA |

|  | 110 | 120 | 130 | 140 | 150 |
|---|---|---|---|---|---|
|  | LVFE<sub>m</sub>APNQE<sub>m</sub>K | VSDYE<sub>m</sub>MKLMD<sub>n</sub> | LDVEQLGIPE | QEYSCVVKMP | SGE<sub>m</sub>FARICRD |
|  | LVFE<sub>m</sub>APNQE<sub>m</sub>K | VSDYE<sub>m</sub>MKLMD | LDVEQLGIPE | QEYSCVVKMP | SGE<sub>m</sub>FARICRD |
|  | APNQE<sub>m</sub>K | VSDYEMKLMD<sub>n</sub> | LDVEQLGIPE | QE<sub>m</sub>YSCVVKMP | SGE |
|  | LVFEAPNQEK | VSDYEMKLMD |  |  |  |

|  | 160 | 170 | 180 | 190 | 200 |
|---|---|---|---|---|---|
|  | LSHIGDAVVI | SCAKDGVKFS | ASGE<sub>m</sub>LGNGNI | KLSQTSNVD<sub>n</sub>K | EEEAVTIEMN |
|  | LSHIGDAVVI | SCAKDGVKFS | ASGE<sub>m</sub>LGNGNI | KLSQTSNVDK | EEEAVTIEMN |
|  |  |  | LGNGNI | KLSQTSNVDK | EEEAVTIEMN |
|  | LSHIG | DGVKFS | ASGELGNGNI | KLSQTSNV |  |

|  | 210 | 220 | 230 | 240 | 250 |
|---|---|---|---|---|---|
|  | E<sub>m</sub>PVQLTFALR | YLNFFTKATP | LSSTVTLSMS | ADVPLVVE<sub>m</sub>YK | IADMGHLKYY |
|  | EPVQLTFALR | YLNFFTKATP | LSSTVTLSMS | ADVPLVVEYK | IADMGHLKYY |
|  | EPVQLTFALR | YLNFFTKATP | LSSTVTLSMS | ADVPLVVE |  |
|  |  |  |  | DVPLVVEYK | IADMGHLKYY |

|  | 260 |  |
|---|---|---|
|  | LAPKIE<sub>m</sub>DEE<sub>m</sub>G | S |
|  | LAPKIE<sub>m</sub>DEEG | S |
|  |  |  |
|  | LAPKIEDEEG | S |

PCNA amino acid sequence

```
         10         20         30         40         50         60
MFEARLVQGS ILKKVLEALK DLINEACWDI SSSGVNLQSM DSSHVSLVQL TLRSEGFDTY 70         80         90        100        110        120
RCDRNLAMGV NLTSMSKILK CAGNEDIITL RAEDNADTLA LVFEAPNQEK VSDYEMKLMD 130        140        150        160        170        180
LDVEQLGIPE QEYSCVVKMP SGEFARICRD LSHIGDAVVI SCAKDGVKFS ASGELGNGNI 190        200        210        220        230        240
KLSQTSNVDK EEEAVTIEMN EPVQLTFALR YLNFFTKATP LSSTVTLSMS ADVPLVVEYK 250        260
IADMGHLKYY LAPKIEDEEG S
```

FIG. 5

CSPCNA ISOFORM MODIFICATIONS AND USES THEREOF

CROSS-REFERENCE TO RELATED APPLICATIONS

This application claims priority to U.S. Ser. No. 60/694,159, filed Jun. 27, 2005.

Part of the work during the development of this invention was made with government support from the Army Medical Research and Material Command under grant DAMD17-02-1-0467. The U.S. Government has certain rights in the invention.

FIELD

The present disclosure relates to detection of malignant cells involving the use of modifications to a cancer specific protein.

BACKGROUND

One of the least understood and most complex disease processes is the transformation that occurs as a cell becomes malignant. This process involves both genetic mutations and proteomic transformations, the result of which, allows the cell to escape normal controls; preventing inappropriate cell division. Cancer cells share some common attributes. Most cancer cells proliferate outside of the normal cell cycle controls, exhibit morphological changes and exhibit various biochemical disruptions to cellular processes.

Cancer is usually diagnosed when a tumor becomes visible well after the first on-set of cellular changes. Many cancers are diagnosed after a biopsy sample is examined by histology for morphologic abnormalities, evidence of cell proliferation and genetic irregularities. Effective treatment for malignancy often depends on the ability to detect reliably, the presence of malignant cells at early stages of a disease so that an effective treatment can begin at a stage when the disease is more susceptible to such treatment. Thus, there is a need to be able to reliably detect a potentially malignant cell that has not progressed to the histological stage recognized as malignant, but which can progress to a malignant state. There is also a need for a rapid, minimally invasive technique that can reliably detect or treat malignant cells or potentially malignant cells.

Proliferating cell nuclear antigen (PCNA) is a 29 kDa nuclear protein and its expression in cells during the S and G2 phases of the cell cycle, makes the protein a good cell proliferation marker. It has also been shown to partner in many of the molecular pathways responsible for the life and death of the cell. Its periodic appearance in S phase nuclei suggested an involvement in DNA replication. PCNA was later identified as a DNA polymerase accessory factor in mammalian cells and an essential factor for SV40 DNA replication in vitro. In addition to functioning as a DNA sliding clamp protein and a DNA polymerase accessory factor in mammalian cells, PCNA interacts with a number of other proteins involved in transcription, cell cycle checkpoints, chromatin remodeling, recombination, apoptosis, and other forms of DNA repair. Besides being diverse in action, PCNA's many binding partners are linked by their contributions to the precise inheritance of cellular functions by each new generation of cells. PCNA may act as a master molecule that coordinates chromosome processing.

PCNA is also known to interact with other factors like FEN-1, DNA ligase, and DNA methyl transferase. Additionally, PCNA was also shown to be an essential player in multiple DNA repair pathways. Interactions with proteins like the mismatch recognition protein, Msh2, and the nucleotide excision repair endonuclease, XPG, have implicated PCNA in processes distinct from DNA synthesis. Interactions with multiple partners generally rely on mechanisms that enable PCNA to selectively interact in an ordered and energetically favorable way.

Clues to a mechanism of PCNA's functions were initially uncovered through investigation of the DNA synthesome, a multiprotein DNA replication complex present in mammalian cells. Studies examining the synthetic activity of the DNA synthesome identified an increased error rate in malignant cells when compared to non-malignant cells. These results suggest that a structural alteration to one or more components of the DNA synthesome in malignant cells has occurred. 2D-PAGE immunoblot analysis of PCNA, an essential component of the DNA synthesome, revealed two distinct isoforms with vastly different isoelectric points (pIs). One PCNA isoform displayed a significantly basic pI and was present in both malignant and non-malignant cells. The other isoform had an acidic pI and was found exclusively in malignant cells. Because of its presence only in malignant cells, this isoform was termed the cancer-specific isoform or csPCNA, and the post-translational alteration that is responsible for PCNA's altered 2D-PAGE migration pattern remains undetermined.

Some labeling studies with PCNA suggested that the migration of PCNA was most likely not due to alterations such as phosphorylation, acetylation, glycosylation, or sialyzation. Conflicting studies have surfaced attempting to identify post-translational modifications to PCNA. For example, the phosphorylation of PCNA was reported to affect its binding to sites of DNA synthesis. Another study claimed that PCNA was, after all, not phosphorylated but acetylated. In addition to these studies, analysis of yeast PCNA has shown it to be the target of ubiquitination in response to DNA damage and sumoylation in the absence of damage. Due to the diverse and conflicting structural evidence for PCNA, it is difficult to identify which modifications, if any, are responsible for the appearance and functions of csPCNA isoform.

Therefore, identification of the correct post-translational modifications of csPCNA is desirable to develop diagnostic methods and also to develop therapeutics based on the interactions of csPCNA with its partners. Malignant cancer cells express an isoform of PCNA termed cancer specific PCNA (csPCNA) and non-malignant cells express an isoform termed non-malignant PCNA (nmPCNA). Effective compositions and methods to distinguish the two isoforms are needed for diagnosis and treatment of cancers.

SUMMARY

Novel post-translational modifications of csPCNA are identified. Methyl esterification of csPCNA is identified. A 2D-PAGE/liquid chromatography tandem mass spectrometry (LC-MS/MS) approach was used to analyze the csPCNA isoform and to identify methyl esterifications present on csPCNA. The methyl esterification modifications were localized to specific glutamic and aspartic acid residues.

A structural analysis of a single acidic PCNA isoform (csPCNA) isolated from breast cancer cells by two-dimensional electrophoresis (2D-PAGE) and liquid chromatography tandem mass spectrometry (LC-MS/MS) is disclosed herein. The methyl esters localized to 16 specific glutamic and aspartic acid residues of csPCNA. The methyl esterification of csPCNA represents a novel type of post-translational modification in mammalian cells that are relevant in addressing some of PCNA's diverse functions.

A method of detecting a cancer specific proliferating cell nuclear antigen (csPCNA) isoform in a biological sample includes the steps of:

detecting a posttranslational modification comprising a methyl ester on one or more amino acid residues of the csPCNA isoform in the sample suspected of containing the csPCNA isoform; and determining the presence of the csPCNA isoform by comparing the levels of methyl esters on the csPCNA isoform with a nonmalignant isoform of PCNA.

Some of the biological samples includes a bodily fluid, such as blood, plasma, lymph, serum, pleural fluid, spinal fluid, saliva, sputum, urine, gastric juice, pancreatic juice, ascites fluid, synovial fluid, milk, and semen.

A biological sample also includes a tissue sample such as tissues obtained from, breast, prostrate, lung, colon, epithelial, connective, cervical, esophageal, brain, thymus, thyroid, pancreas, testis, ovary, intestine, bladder, stomach, soft tissue sarcomas, osteosarcoma, leukemia, lymphoma, carcinoma, adenocarcinoma, placenta, fibrous, germ cell tissue, and extracts thereof. Any biological sample that is capable of containing csPCNA is suitable for analysis.

In an aspect, the methyl ester is present on an aspartic acid or on a glutamic acid or a combination thereof of the csPCNA isoform. A methyl ester is present on one or more of the 16 aspartic acid or glutamic acid residues on the csPCNA isoform. The methyl ester present on one or more of the 16 aspartic acid or glutamic acid residues correspond to the amino acid positions with reference to SEQ ID NO: 30 of 3, 85, 93, 94, 104, 109, 115, 120, 132, 143, 174, 189, 201, 238, 256, and 259 of csPCNA isoform. The csPCNA-derived peptides that include the 16 aspartic acid or glutamic acid modified residues are as follows:

MFE$_m$AR (SEQ ID NO: 1);
IE$_m$DEEGS (SEQ ID NO: 2);
IEDEE$_m$GS (SEQ ID NO: 3);
VSDYE$_m$MK (SEQ ID NO: 4);
MPSGE$_m$FAR (SEQ ID NO: 5);
LSQTSNVD$_m$K (SEQ ID NO: 6);
CAGNE$_m$DIITLR (SEQ ID NO: 7);
FSASGE$_m$LGNGNIK (SEQ ID NO: 8);
AEDNADTLALVFEAPNQE$_m$K (SEQ ID NO: 9);
AE$_m$DNADTLALVFEAPNQEK (SEQ ID NO: 10);
AED$_m$NADTLALVFEAPNQEK (SEQ ID NO: 11);
AEDNADTLALVFE$_m$APNQEK (SEQ ID NO: 12);
LMD$_m$LDVEQLGIPEQEYSCVVK (SEQ ID NO: 13);
ATPLSSTVTLSMSADVPLVVE$_m$YK (SEQ ID: 14);
LSQTSNVDKEEEAVTIEMNE$_m$PVQLTFALR (SEQ ID NO: 15); and
LMDLDVEOLGIPEOE$_m$YSCVVK (SEQ ID NO: 31),
wherein E$_m$ represents a methylesterified glutamic acid residue and D$_m$ represents a methylesterified aspartic acid residue.

In an aspect, the detection of csPCNA isoform is performed using a mass spectrometric analysis, for example, by liquid chromatography (LC) mass spectrometric (MS) analysis. Any suitable method of detection of methyl esters or methylesterified amino acid residues is applicable.

A mass spectrometric analysis of a csPCNA-derived peptide results in a 14 Da mass shift as compared to a corresponding unmodified peptide.

A method of diagnosing or prognosing malignancy, the method includes the steps of:

detecting cancer specific proliferating cell nuclear antigen (csPCNA) isoform isoform in a biological sample by identifying a posttranslational modification state of csPCNA isoform that distinguishes the csPCNA isoform from a nonmalignant PCNA (nmPCNA) isoform; and diagnosing malignancy based on the detection of csPCNA in the biological sample.

A posttranslational modification such as methylesterification is detected on csPCNA and the methylesterification levels on csPCNA versus nmPCNA are used in determining malignancy.

A modified proliferating cell nuclear antigen (PCNA) peptide includes an amino acid sequence selected from:

MFE$_m$AR (SEQ ID NO: 1);
IE$_m$DEEGS (SEQ ID NO: 2);
IEDEE$_m$GS (SEQ ID NO: 3);
VSDYE$_m$MK (SEQ ID NO: 4);
MPSGE$_m$FAR (SEQ ID NO: 5);
LSQTSNVD$_m$K (SEQ ID NO: 6);
CAGNE$_m$DIITLR (SEQ ID NO: 7);
FSASGE$_m$LGNGNIK (SEQ ID NO: 8);
AEDNADTLALVFEAPNQE$_m$K (SEQ ID NO: 9);
AE$_m$DNADTLALVFEAPNQEK (SEQ ID NO: 10);
AED$_m$NADTLALVFEAPNQEK (SEQ ID NO: 11);
AEDNADTLALVFE$_m$APNQEK (SEQ ID NO: 12);
LMD$_m$LDVEQLGIPEQEYSCVVK (SEQ ID NO: 13);
ATPLSSTVTLSMSADVPLVVE$_m$YK (SEQ ID NO: 14);
LSQTSNVDKEEEAVTIEMNE$_m$PVQLTFALR (SEQ ID NO: 15); and
LMDLDVEQLGIPEQE$_m$YSCVVK (SEQ ID NO: 31),
wherein E$_m$ represents a methylesterified glutamic acid residue and D$_m$ represents a methylesterified aspartic acid residue.

In one aspect, the modified peptides of csPCNA or PCNA are posttranslationally modified. In another aspect, the modified peptides of csPCNA or PCNA are exposed to a protease digestion step. In another aspect, the modified peptides of csPCNA or nmPCNA are synthetic.

In an aspect, a method of detecting a cancer specific proliferating cell nuclear antigen (csPCNA) isoform in a biological sample includes determining the overall methylesterification levels of csPCNA and nmPCNA and determining that the biological sample has csPCNA based on the methylesterification levels.

Additional features of the present disclosure will become apparent to those skilled in the art upon consideration of the following detailed description of embodiments exemplifying the best mode of carrying out the subject matter of the disclosure as presently perceived.

BRIEF DESCRIPTION OF THE DRAWINGS

FIG. 5 shows an amino acid sequence of PCNA (1-261 amino acids).

DETAILED DESCRIPTION

Figure 1D:
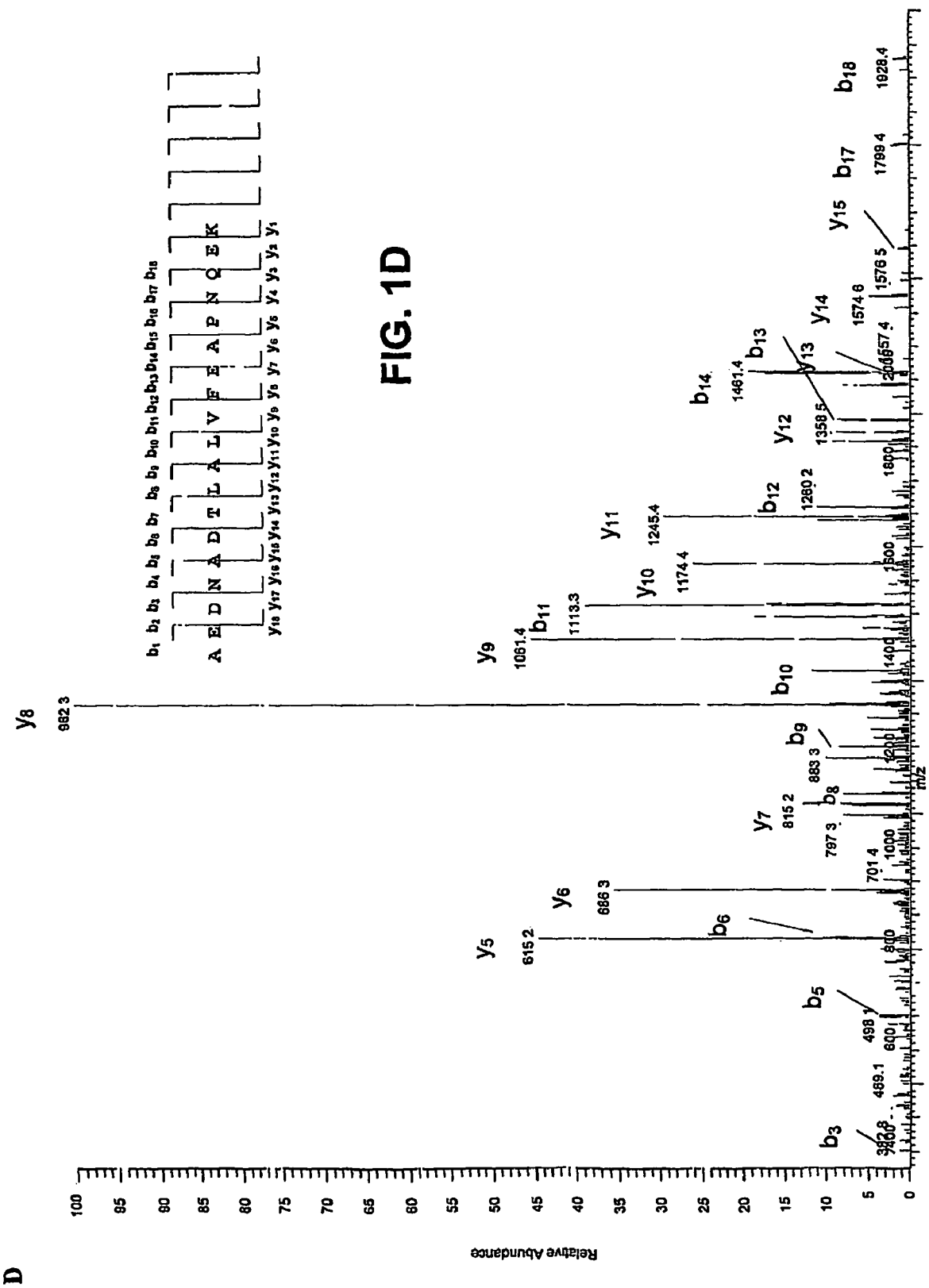
FIG. 1 demonstrates identification of csPCNA from 2D-PAGE by LC-MS/MS peptide characterization. (A) shows a representative Coomassie blue stained 2D-PAGE gel of a MDA MB 468 cell nuclear extract (2 mg). Multiple spots were chosen for proteolysis with trypsin and identified by LC-MS/MS. csPCNA is identified (black arrow) on the acidic side of the gel with an approximate pI of 4.6. Three dimensional representation of the 2D-PAGE detects two spots corresponding to csPCNA, a spot of modest abundance (black arrow), and a more acidic spot of low abundance (white arrow) detected by the 2D analysis software. Protein spots (i-v) other than PCNA that were identified in the analysis are presented in Table I. (B) shows base peak chromatogram of the peptides derived from the trypsin digestion of csPCNA. (C) illustrates mass spectrum of a csPCNA peptide eluting at 43.3 min. Analysis of the tandem mass spectrum of the 1038.7 m/z ion (D) identified it as a doubly charged peptide corresponding to residues 92-110 of human PCNA. (E) is mass spectrum showing the elution of a 1045.4 m/z ion at 43.74 min. The mass difference of the singly charged ions is twice the difference of the doubly charged ion and the 1045.4 m/z ion therefore displays a +14 Da mass shift. (F) shows tandem mass spectrum of the 1045.4 m/z ion is nearly identical to the one in part D except that all of the y-ions are shifted by 14 Da. The shift in mass of only the $b_{18}$-ion locates the additional 14 Da on the glutamic acid at position 109 of csPCNA.

Proliferating cell nuclear antigen (PCNA) protein is altered in cancer cells. PCNA is a 28 kD protein with an electrophoretic mobility equivalent to that of a 36 kDa protein. PCNA is an accessory factor required by DNA polymerase δ to mediate highly efficient DNA replication activity. The DNA synthesome purified from a malignant cell contains at least two forms of PCNA. The two species of PCNA differ significantly in their overall charge. Thus, an acidic, malignant or cancer specific, form of PCNA, csPCNA, and a basic, nonmalignant or normal, form of PCNA, nmPCNA, can be distinguished on a two-dimensional polyacrylamide gel.

The acidic csPCNA is expressed in malignant cell lines, such as HeLa (human cervical carcinoma), Hs578T (breast carcinoma), HL-60 (human promyelogenous leukemia), FM3A (mouse mammary carcinoma), PC 10 (prostate carcinoma), LNCaP (prostate carcinoma), LN99 (prostate carcinoma) MD-MB468 (human breast carcinoma), MCF-7 (breast carcinoma), KGE 90 (esophageal-colon carcinoma), KYE 350 (esophageal-colon carcinoma), SW 48 (esophageal-colon carcinoma) and T98 (malignant glioma). The acidic csPCNA is also expressed in malignant cells obtained from human breast tumors, prostate tumors, brain tumors, human gastrointestinal or esophageal-colon tumors, murine breast tumors and in human chronic myelogenous leukemia. The acidic csPCNA is not detected in nonmalignant cell lines, such as the breast cell lines Hs578Bst and MCF-10A, or in samples of nonmalignant serum or tissue, such as breast.

An LC-MS/MS peptide characterization approach was used to sequence a csPCNA isoform found in malignant cells. A novel type of post-translational modification present on numerous residues of csPCNA was identified. This modification, methyl esterification, was present on 16 different aspartic acid and glutamic acid residues in csPCNA. Unmodified amino acid sequence of PCNA is shown in FIG. 5. These methyl esters were initially identified as 14 Da shifts in peptide mass and were localized to either glutamic or aspartic acid residues by tandem mass spectrometry. Relative quantitation of the methyl esterified peptides indicated that csPCNA proteins in malignant cells include several molecules containing one or more methyl esters that occur at multiple residues throughout the protein. Methyl esterification of specific residues is likely to result in discrete conformational changes in the protein, and these changes may promote and/or disrupt protein/protein interactions.

The effects of methyl esterification on mammalian protein functions are poorly understood. Much of the past research into methyl esterification of mammalian proteins has focused on protein aging and the repair of isoaspartyl residues by the enzyme protein isoaspartate methyl transferase (PIMT). However, most methyl esters present on csPCNA are found on glutamic acid residues and not aspartic acid residues suggesting that the modification occurs via an alternate pathway.

It is possible that methyl esterification of PCNA alters its conformation and, in effect, hide and/or expose specific protein binding sites and determines its function. LC-MS/MS sequence analysis of recombinant PCNA was also performed and evidence for methyl esterification was found. The methyl esterification found on PCNA may therefore stabilize specific conformational states of an otherwise disordered protein. Additionally, calculation of the electrostatic potential of PCNA shows that the outer surface of the PCNA trimer has a highly negative potential and an abundance of glutamic and aspartic acid residues. Methylation of these residues could therefore alter this potential and, in effect, change the surface topology of the protein.

LC-MS/MS peptide characterization of a specific isoform, csPCNA, resolved by 2D-PAGE is disclosed. Using a combination of proteolytic approaches, staggered peptide sequence maps of csPCNA were generated, identifying 100% of the csPCNA protein sequence by LC-MS/MS. A novel post-translational modification present on csPCNA was identified. Methyl esters appeared on at least one of 16 specific aspartic and/or glutamic acid residues in the csPCNA isoform. These modifications, may alter the structure of the PCNA trimer and by doing so promote conformational changes that may be relevant for ordered protein/protein interactions.

A biological sample can be a body fluid sample, which may include blood, plasma, lymph, serum, pleural fluid, spinal fluid, saliva, sputum, urine, semen, tears, synovial fluid or any bodily fluid that can be tested for the presence of csPCNA isoform. Alternatively, the biological sample can be a tissue sample, wherein the cells of the tissue sample may be suspected of being malignant. For example, tissue sections or cell cultures can be mounted on glass or plastic slides and contacted with the antibodies according to standard immunocytochemical protocols. Tissue extracts or concentrates of cells or cell extracts are also suitable.

In another embodiment, a method for diagnosing malignancy is provided. The method comprises the step of detecting csPCNA in a biological sample obtained from a person or particularly a patient suspected of having a malignant condition, wherein the detecting csPCNA step involves detecting levels of posttranslational modification involving methylesters disclosed herein.

In another embodiment, a method to aid in diagnosing malignancy is provided. The method comprises the step of detecting posttranslational modifications on csPCNA in malignant cells in a tissue sample compared to PCNA in normal cells, wherein cells of the tissue sample are suspected of being malignant, and wherein the detecting csPCNA step involves detecting methyl esters on csPCNA. It is to be understood that the malignant cells are not limited to, malignant cells in tissues such as breast, prostate, blood, brain, pancreas, smooth or striated muscle, liver, spleen, thymus, lung, ovary, skin, heart, connective tissue, kidney, bladder, intestine, stomach, adrenal gland, lymph node, or cervix, or in cell lines, for example, Hs578T, MCF-7, MDA-MB468, HeLa, HL60, FM3A, BT-474, MDA-MB-453, T98, LNCaP, LN 99, PC 10, SK-OV-3, MKN-7, KGE 90, KYE 350, or SW 48.

In another embodiment, a method to aid prognosis of the development of malignancy is provided. The method involves detecting csPCNA in a tissue sample by detecting posttranslational modifications disclosed herein, wherein cells of the tissue sample may be suspected of being malignant, and correlating the levels of csPCNA with the progression of a particular malignant disease. Furthermore, the detection and analysis of posttranslational modifications on csPCNA can be used to prognose the potential survival outcome for a patient who has developed a malignancy.

It is to be understood that the diseases which can be diagnosed or prognosed using the antibodies include, but are not limited to, malignancies such as various forms of glioblastoma, glioma, astrocytoma, meningioma, neuroblastoma, retinoblastoma, melanoma, colon carcinoma, lung carcinoma, adenocarcinoma, cervical carcinoma, ovarian carcinoma, bladder carcinoma, lymphoblastoma, leukemia, osteosarcoma, breast carcinoma, hepatoma, nephroma, adrenal carcinoma, or prostate carcinoma, esophageal carcinoma. If a malignant cell expresses csPCNA isoform, the techniques disclosed herein are capable of detecting the csPCNA isoform.

Detection techniques involving the detection of posttranslational modifications disclosed herein, could also detect malignancy in some of the invasive and non-invasive tumor types in breast tissue that includes ductal cysts, apocrine metaplasia, sclerosing adenosis, duct epithelial hyperplasia, non-atypical, intraductal papillomatosis, columnar cell changes, radial sclerosing lesion (radial scar), nipple adenoma, intraductal papilloma, fibroadenoma, lactating papilloma, atypical duct epithelial hyperplasia, atypical lobular hyperplasia, ductal carcinoma in situ-sub classified as nuclear grades 1, 2, and 3, lobular carcinoma-in-situ, pleomorphic lobular carcinoma-in-situ, intra-mammary lipoma, mammary hamartoma, granular cell tumor, intramammary fat necrosis, pseudoangiomatous stromal hyperplasia (PASH), malignant melanoma involving the breast, malignant lymphoma involving the breast, phyllodes tumor—benign, borderline, and malignant subclasses, and sarcoma of the breast.

In another embodiment, methods disclosed herein are used to determine the malignancy stage in tumors, by comparing levels of csPCNA in a tumor over time, to follow the progression of a malignant disease, or a patient's response to treatment. The methods can also be used to detect malignant cells which have broken free from a tumor and are present in a patient's bloodstream, by methods to assay a blood sample for the presence of the csPCNA isoform. The biological sample can be obtained from human patients or veterinary patients.

The term "antibody" includes monoclonal antibodies (including full length monoclonal antibodies), polyclonal antibodies, multispecific antibodies (e.g. bispecific antibodies), and antibody fragments so long as they exhibit the desired biological activity or specificity.

Antibodies that specifically recognize posttranslationally modified nmPCNA or csPCNA can be made.

The term "modified protein or peptide" refers to the presence of one or more posttranslational modifications present on csPCNA or nmPCNA proteins or peptides derived from these proteins. The term also refers to synthetic and isolated and purified peptides of csPCNA and nmPCNA that contain one or more posttranslational modifications. The term also refers to protease digested peptides of csPCNA and PCNA and peptides of csPCNA and PCNA fragmented by any known methods that contain one or more posttranslational modifications.

All chemicals used herein were obtained from Sigma-Aldrich (St Louis, Mo.) or Fisher Scientific (Hampton, N.H.) unless otherwise stated. Mass spectrometry grade water and acetonitrile were obtained from Honeywell Burdick and Jackson (Morristown, N.J.).

csPCNA and nmPCNA present in samples obtained from individuals are analyzed for posttranslational modifications using any standard technique. For example, mass spectrometric analyses is a suitable technique. Mass spectrometric analysis can be coupled with other techniques.

MDA MBA 468 and MCF7 breast cancer cells were obtained from ATCC and maintained in DMEM (MediaTech, Hemdon, Va.) containing 10% FCS (BioWhittaker, Walkersville, Md.) and Antibiotic-Antimycotic (Invitrogen, Carlsbad, Calif.). Cells were grown on 100 mm cell culture dishes until 60-70% confluent, rinsed and scraped with a rubber policeman into ice-cold PBS prior to pelleting. Cells were fractionated to a nuclear extract as described in Malkas et al., *Biochemistry* 1990, 29, 6362-6374. Briefly, the cells were homogenized using a Dounce™ homogenizer and the nuclei pelleted. Nuclear proteins were subsequently extracted with 150 mM KCl for 2 h at 4° C. and membranes pelleted by ultracentrifugation. Nuclear extracts were frozen at −80° C. until use.

Isoelectric focusing was performed using an IEF cell and 17 cm pH 4-7 Ready Strip IPG strips (Bio-Rad, Hercules, Calif.). Protein samples were desalted using Protein Desalting Spin Columns (Pierce, Rockford, Ill.) and lyophilized in a speed-vac (ATR Biotech, Laurel, Md.). Lyophilized samples were re-suspended in rehydration buffer (9 M urea, 4% CHAPS, 0.2% Bio-Lytes (Bio-Rad, Hercules, Calif.), 2 mM tributylphosphine, 0.001% bromophenol blue) and passively rehydrated into the IPG strips for 12 h at 20° C. Isoelectric focusing was carried out following the manufacturer's instructions (Bio-Rad, Hercules, Calif.). Prior to SDS-PAGE, the IPG strips were reduced by incubation in buffer (6 M urea, 0.375 M tris, 2% SDS, 20% glycerol, pH 8.8) containing 20 mg/ml DTT and alkylated in same buffer containing iodoacetamide in place of DTT. SDS-PAGE was performed on 12% polyacrylamide gels (20 cm×20 cm) using a Protean XL apparatus (Bio-Rad, Hercules, Calif.) with constant current for approximately 5 h. Gels were fixed with 10% acetic acid/50% methanol in water and stained with Gel Code Blue (Pierce, Rockford, Ill.) overnight. Imaging was accomplished using a GS710 Scanning Image Densitometer (Bio- Rad, Hercules, Calif.) and gel analysis was carried out with Phoretix Evolution 2D software (NonLinear Dynamics, Inc., Durham, N.C.). Spot picking was done manually using a 1 mm coring tool (The Gel Company, San Francisco, Calif.).

Protein cleavage was performed with trypsin (Promega, Madison, Wis.), cyanogen bromide (CNBr) (Sigma-Aldrich, St. Louis, Mo.), GluC, or AspN (Roche, Indianapolis, Ind.) as previously described with some modification (Rosenfeld et al., Anal Biochem 1992, 203, 173-179; van Montfort et al., Biochim Biophys Acta 2002, 1555, 111-115). Briefly, gel spots were destained in 25 mM ammonium bicarbonate (ABC)/50% acetonitrile followed by dehydration with 100% acetonitrile and drying in a speed-vac (ATR Biotech, Laurel, Md.). Spots were then rehydrated in protease solution (20 µg/ml of either trypsin, GluC, or AspN) in 25 mM ABC. After 10 min at 4° C., excess protease solution was removed, replaced with fresh 25 mM ABC, and incubated overnight at 37° C. Peptides were extracted from the gel by sonication in the presence of 25 mM ABC/50% acetonitrile (once) and 5% formic acid/50% acetonitrile (twice). The peptide extracts were pooled and dried in a speed-vac. Subsequent CNBr cleavages of trypsin digests (on selected samples) were carried out by re-suspending the dried peptide extracts in 70% formic acid and adding CNBr to approximately a 200 M excess relative to the peptide. CNBr cleavage was carried out at room temperature for 4 h and dried in the speed-vac. All samples were re-suspended in 1% formic acid immediately prior to analysis.

Nanoflow HPLC was performed using an IntegraFrit (New Objective, Inc., Woburn, Mass.) trapping column packed in-house with Magic C18Aq 5µ, 200 Å (Michrom, Inc., Auburn, Calif.) and a 0.05 mm×100 mm pulled-tip fused silica column (PolymicroTechnologies, Phoenix, Ariz.) self-packed with Magic C18Aq 5µ, 100 Å material and mounted on a micro-cross held in place by a custom nanospray stage (Gatlin et al., Anal Biochem 1998, 263, 93-101). Peptides were separated using a 2-50% linear gradient of acetonitrile containing 0.1% formic acid. Instrumentation consisted of either a Surveyor HPLC and LCQ Advantage ion trap mass spectrometer (ThermoElectron, Waltham, Mass.) or an Ultimate HPLC (LC Packings) and a LCQ DECA XP (ThermoElectron, Waltham, Mass.). Peak lists were generated from the raw data using BioWorks 3.1 (ThermoElectron, Waltham, Mass.). Swissprot database searching was performed using Mascot (Matrix Science, Inc., Boston, Mass.)(See also, Creasy & Cottrell, Proteomics 2002, 2, 1426-1434). Parent ion and fragment mass tolerance of 3 and 0.8 Da, respectively, and up to two missed cleavage sites were considered. Carbamidomethyl cysteines and oxidized methionines were selected as variable modifications in a first pass search of the mammalian database. A subsequent error tolerant search was performed where trypsin was selected as the enzyme and glutamate and aspartate methyl esters were additionally considered as variable modifications.

While the methods of detecting posttranslational modification and uses thereof relating to the csPCNA isoform have been described in detail in the detailed description and in the Examples below, and with reference to specific embodiments thereof, it will be apparent to one with ordinary skill in the art that various changes and modifications can be made therein without departing from the spirit and scope thereof. All references cited herein are incorporated by reference in their entirety.

EXAMPLES

The following examples are provided for the purpose of exemplification only and are not intended to limit the disclosure which has been described in broad terms above.

Example 1

Two-Dimensional (2D) Page and Peptide Characterization of csPCNA Isoform

A nuclear extract fraction isolated from MDA MB 468 breast carcinoma cells was resolved by 2D-PAGE (FIG. 1A). Multiple spots having apparent molecular masses near 36 kDa and pIs at or near 4.5 (PCNA's apparent SDS-PAGE MW and calculated pI) were excised from the gel and subjected to in-gel digestion with trypsin. The resulting peptides were analyzed by nanoflow liquid chromatography (C) and electrospray tandem mass spectrometry (LC-MS/MS) using a quadrupole ion trap mass spectrometer. The proteins comprising each spot were identified by searching the tandem MS data with the Mascot search engine. Using this approach csPCNA was localized on 2D-PAGE gels. This approach allowed routine identification and analysis of csPCNA with limited sample handling thus minimizing potential loss of post-translational modifications. FIG. 1B shows a representative base peak LC/MS chromatogram of peptides resulting from the in-gel trypsin digestion of csPCNA excised from 2D-PAGE gels. In this experiment 25 peptides covering 97% of the full-length PCNA sequence were identified. A representative csPCNA peptide identified in this experiment is shown in FIG. 1C. This peptide eluted at 43.3 min and displayed an m/z of 1038.7 (2+) (FIG. 1C). Collision induced dissociation (CID) of the peptide (Roepstorff, P. and Fohlnan, J., Biomed Mass Spectrom 1984, 11, 601) revealed the sequence AEDNADTLALVFEAPNQEK, amino acids 92-110 of human PCNA (FIG. 1D).

Example 2

The Methyl Esterification of csPCNA

Figure 1F:
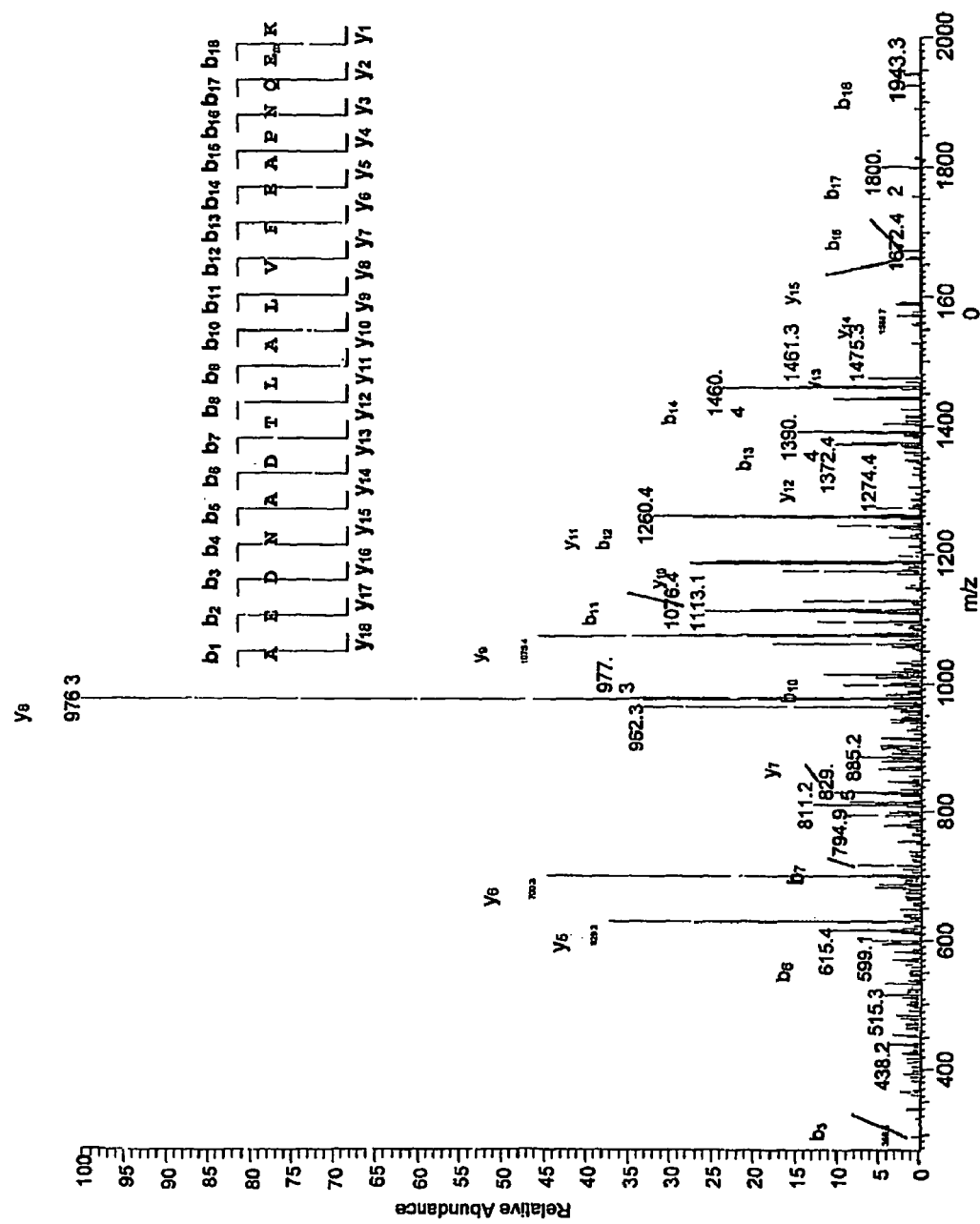

This example demonstrates that csPCNA isoform displays methyl esterification at one or more amino acid locations. The LC-MS/MS data identified multiple peptides displaying a 14 Da shift in parent peptide mass. Interestingly, the identified mass shifts suggested the presence of a post-translational modification—methyl esterification. Methylation in mammalian cells is generally considered an irreversible post-translational modification. Occurring predominantly on the amine groups of lysine residues and the N-termini of proteins, methylation has been identified on proteins such as p53 and histones H3 and H4. However, examination of the CID spectra for the +14 Da shifted peptides localized the methyl groups to aspartic and glutamic acid residues consistent with methyl esterification. FIG. 1E shows the elution of a methyl esterified peptide (1045.4 m/z [2+]) at 43.8 min in this experiment. This peptide eluted close to (25 sec after) the unmodified 1038.7 m/z (2+) peptide (FIG. 1C), which can still be seen in the MS spectrum. Fragmentation of the 1045.4 m/z ion (FIG. 1F) uncovered a pattern very similar to the 1038.7 m/z peptide (FIG. 1D). The major difference in these fragmentation spectra are +14 mass shifts in nearly all of the y-series ions of the 1045.4 m/z peptide compared to the y-series ions of the 1038.7 m/z peptide. Inspection of the high MW region of the 1045.4 CID spectrum (FIG. 1F) identifies two b-ions with m/z values of 1943.3 and 1800.2. The 1943.3 ion corresponds to the $b_{18}$-ion and indicates a loss of an unmodified lysine from the C-terminus. This ion also differs from the $b_{18}$-ion (1928.4) observed in the fragmentation spectrum of the 1038.7 m/z peptide (FIG. 1D) by 14 Da further suggesting that the lysine is unmodified and the 14-Da mass shift is on another residue in the peptide. The $b_{17}$-ion (1800.2) in FIG. 1F, on the other hand, closely matches the $b_{17}$-ion (1799.4) in FIG. 1D indicating the loss of a glutamic acid (129 Da) plus a methyl group (14 Da) or a 143 Da loss between the $b_{17}$ and $b_{18}$-ions for the 1045.4 m/z peptide. The small peaks just to the left of the $b_{18}$-ions in FIGS. 1D and 1F have m/z values of 1911.1 and 1925.4, respectively, consistent with a neutral loss of $H_2O$ or $NH_3$ from the $b_{18}$-ions. These observations in combination with the shifted y-ion masses localize the methyl ester to the glutamic acid residue at position 109 in the full-length csPCNA protein.

In addition to csPCNA, other proteins in the gel were analyzed for the presence of methyl esterification. Five representative protein spots are shown in FIG. 1A, and the identities of these spots and their methyl esterification status are presented in Table I. Interestingly, one of the five proteins (Stathmin) analyzed was found to be methyl esterified as well as N-terminally acetylated. Methyl esterification of csPCNA was not the result of sample handling (e.g. gel fixation with acetic acid and methanol), because methyl esterification was observed on only a small subset of proteins, and consistently on specific csPCNA residues, instead of its presence throughout all of the proteins present in the gel.

Example 3

Identification of Methylesterification of csPCNA

Figure 2A:
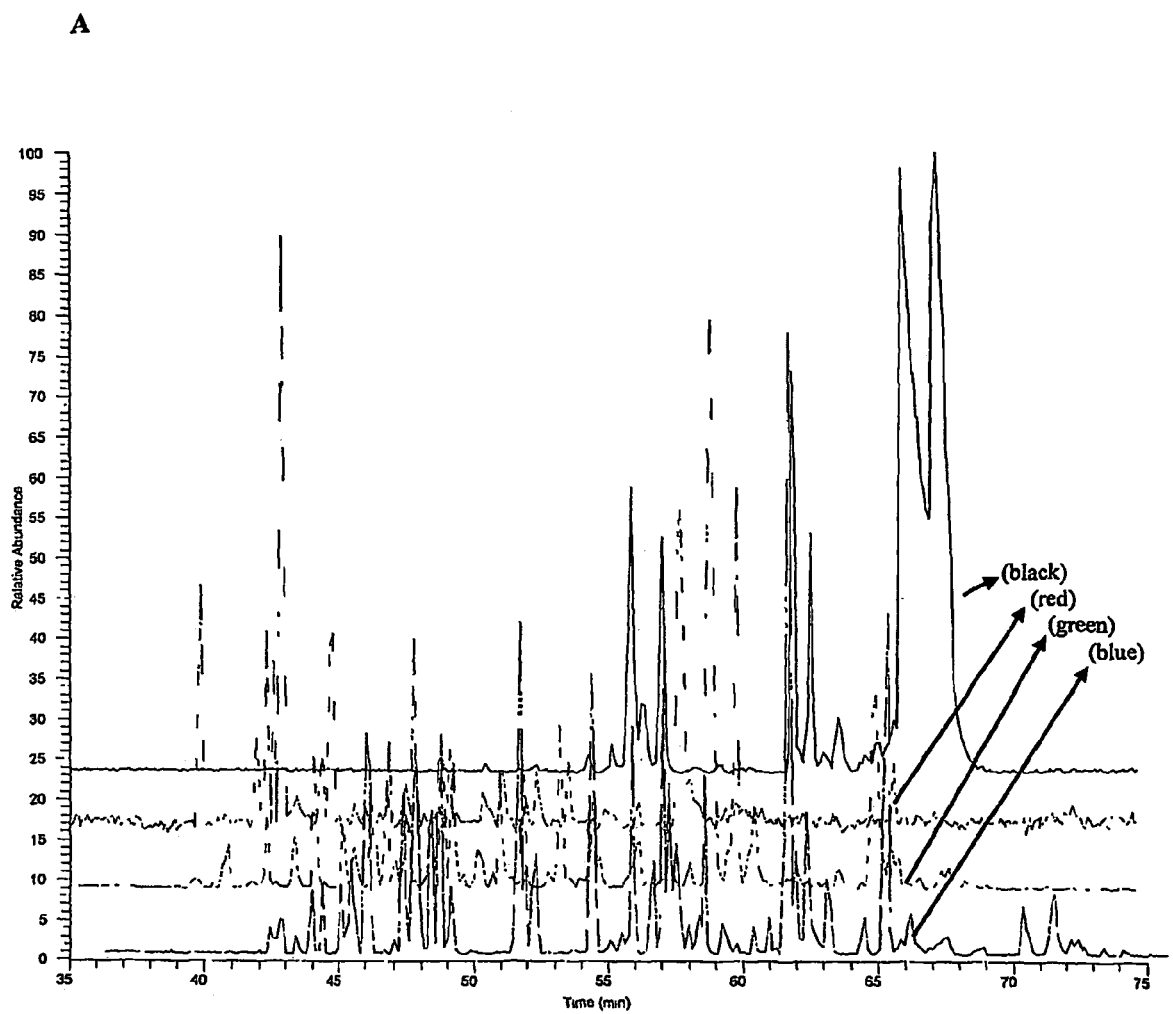
FIG. 2 shows creation of staggered peptide sequence maps of csPCNA. (A) Representative base peak chromatograms showing the elution of peptides derived from the cleavage of csPCNA with trypsin (blue), trypsin/CNBr (green), GluC (Ted), and AspN (black). (B) csPCNA maps of sequences identified by LC-MS/MS. The locations of methyl esters are denoted ($X_m$).

In addition to the AEDNADTLALVFEAPNQEK peptide identified in FIG. 1, multiple other csPCNA peptides consistently displayed 14 Da mass shifts. To successfully identify all sites of methyl esterification, as well as identify any other potential post-translational modifications present on the csPCNA isoform, staggered peptides were generated utilizing different reagents as shown in sequence maps of the csPCNA isoform. FIG. 2A shows representative base peak chromatograms of LC-MS/MS experiments derived from separately digesting csPCNA with trypsin alone, trypsin followed by cyanogen bromide (CNBr) cleavage, AspN alone, or GluC alone. These base peak traces show the differences in the elution profiles for the peptides generated using these techniques. Digestion with trypsin alone and trypsin and CNBr provided sequence coverage and the AspN and GluC experiments provided additional confirmatory data. CNBr cleavage, which cuts C-terminal to methionine residues, reduced the size of larger tryptic peptides making those sequences amenable to LC-MS/MS analysis using the ion trap. This combined digestion was useful in characterizing the 33-residue tryptic peptide DLINEACWDISSSGVN-LQSM DSSHVSLVQLTLR (PCNA residues 21-53). Digestion with AspN and GluC generated confirmatory data although it did not generate full sequence coverage. This is likely due to multiple factors. For example, GluC and AspN have a smaller number of cleavage sites in PCNA as compared to trypsin and therefore generate larger peptides that are more difficult to analyze. Additionally, these proteases recognize aspartic and glutamic acid residues in proteins, the same residues found in this study to be methyl esterified. Therefore, methyl esterification could potentially affect protease cleavage producing larger peptides and ultimately leading to poor sequence coverage. This loss of protease cleavage can be used as a diagnostic tool to detect methyl esterification.

The peptides generated with a protonated C-terminal residue like tryptic peptides generally produce good quality CID spectra. Combined data generated from multiple sequencing experiments using these different approaches consistently identified 16 methyl esterified glutamic and aspartic acid residues on csPCNA from MDA MB 468 and MCF7 breast cancer cells (see Table III). The resulting sequence maps of csPCNA are presented in FIG. 2B along with any modifications identified by LC-MS/MS. In addition to methyl esterification, several other modifications were observed. Oxidized methionines and carbamidomethyl cysteines were consistently observed on csPCNA and other proteins in all of the experiments. Additionally, multiple "formylated" serines, threonines, and tyrosines were observed in the trypsin/CNBr digests. However, these modifications are likely chemical modifications that result from sample handling and are not "native" post-translational modifications.

Example 3A

Identification of Other Posttranslational Modifications on PCNA and csPCNA

In addition to identifying methyl esters on csPCNA, the entire csPCNA molecule was analyzed for the presence of other known post-translational modifications. In contrast to previous reports on other forms of PCNA, ubiquitination, sumoylation, phosphorylation, or acetylation were not identified on csPCNA. Ubiquitination and sumoylation would lead to a significant mass shift in PCNA on 2D-PAGE gels, which are not observed with the csPCNA isoform. Also, no peptides corresponding to either ubiquitination or sumoylation were identified in any of the LC-MS/MS experiments of csPCNA, and no csPCNA peptides displayed mass shifts consistent with ubiquitin or sumoylation conjugation strongly indicating that csPCNA in the gel spots analyzed here were neither ubiquitinated nor sumoylated. And although PCNA was previously reported as phosphorylated, no data supporting the phosphorylation of any residues of csPCNA was found in these analyses. None of the csPCNA peptides observed in these analyses demonstrated a +80 Da mass shift and/or a neutral loss if $H_3PO4$ (98 Da), which is consistent with reports showing that PCNA is acetylated and not phosphorylated. Additionally, the gels were immunoblotted for the presence phosphoserine, phosphothreonine, phosphotyrosine, acetylated lysine, as well as poly (ADP) ribose and were unable to detect these post-translational modifications on PCNA.

The csPCNA isoform in breast cancer cells is not phosphorylated, acetylated, ubiquitinated, or sumoylated, but is instead methyl esterified. Similar to acetylation and phosphorylation, methyl esterification could change its migration on 2D-PAGE. However, unlike acetylation and phosphorylation, which would shift the molecule to a more acidic pI, methyl esterification would cause the protein to resolve at a more basic pI. It could therefore be postulated that the low abundance acidic isoform seen in FIG. 1A (white arrow) may be an isoform that contains fewer or no methyl esters as compared to the csPCNA isoform.

The csPCNA isoform contains a low amount of methyl esterification compared to the normal or non-malignant form of PCNA (nmPCNA or simply PCNA). The non-malignant or basic PCNA isoform likely contains a higher level of methyl esterification. This conclusion is based, in part, on the fact that methyl esterification modifies acidic residues and would shift the protein to a more basic pI (due to loss of acidic charge) and the csPCNA isoform is very close to its calculated pI of 4.5.

However, acetylation, phosphorylation and ADP-ribosylation would shift a protein to a more acidic pI below 4.5 (due to addition of an acidic charge). Therefore, these modifications are not likely responsible for the pI shift. Measuring the extent of methyl esterification on PCNA and csPCNA determines malignant from non-malignant (csPCNA from nmPCNA). Using the methods disclosed herein, the methylesterification levels of csPCNA and nmPCNA are determined and compared for diagnosis of malignancy. For example, Table II provides methylesterification state of various csPCNA-derived peptides and the % modified in a heterogeneous population. Table II can be used as a comparison chart for determining the various methylesterification levels in diagnosing malignancy.

Example 4

Semi-Quantitation of Methyl Esterified csPCNA Peptides

Figure 3A:
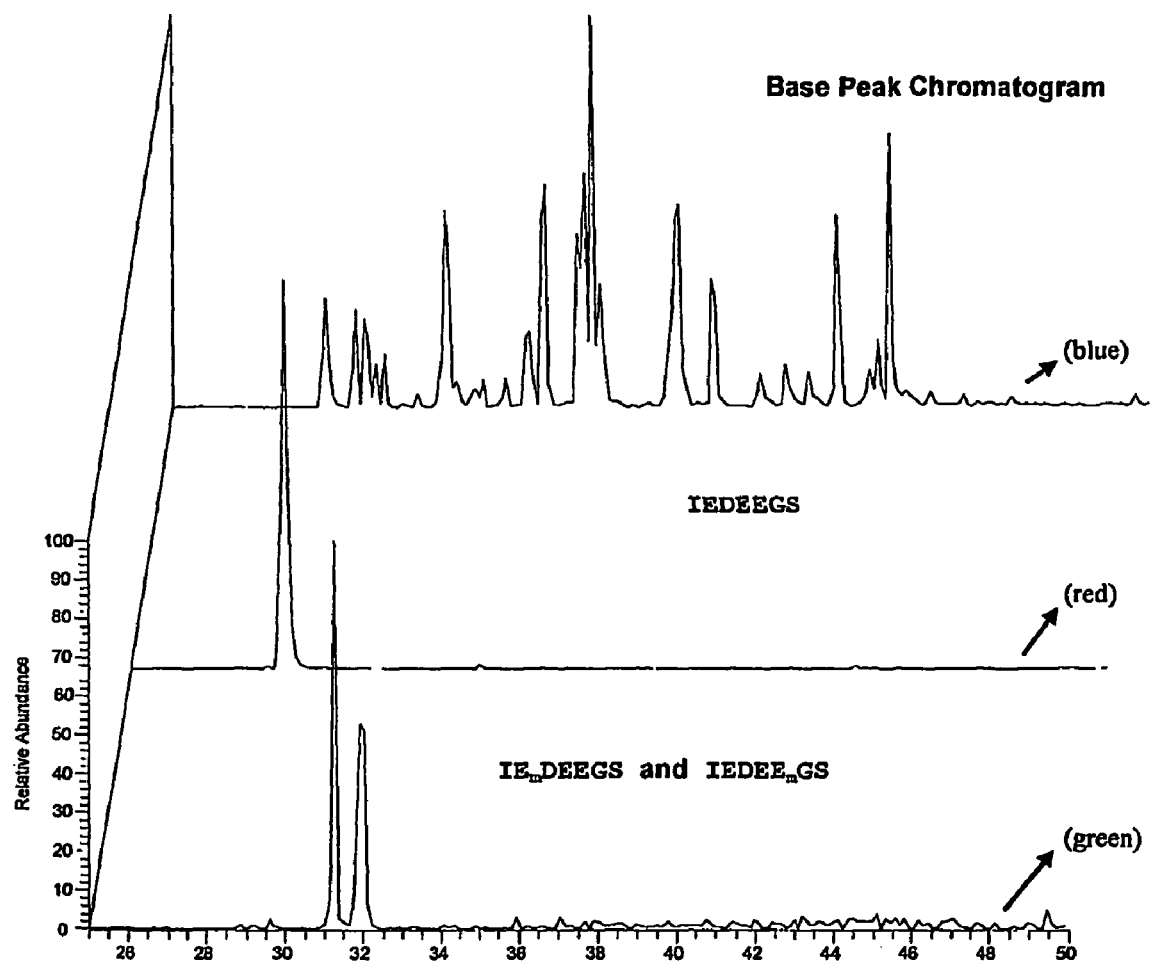
FIG. 3 shows that the C-terminal tail of PCNA is methyl esterified at multiple sites. (A) Elution of three different peptides derived from the C-terminal tail of csPCNA. The base peak chromatogram of csPCNA digested with trypsin compared to the selected ion chromatograms of the peptide IEDEEGS (778.5 m/z) and the methyl esterified IEDEEGS peptides (792.5). The methyl esterified peptides have an increased hydrophobicity and elute later in the reversed-phase gradient. (B) Interpretation of the tandem mass spectra for the unmodified peptide shows the fragmentation of a singly charged peptide with the sequence IEDEEGS. The neutral loss of water (−18 Da) is commonly observed with many of the fragment ions. Additionally, a fragment ion representing the neutral loss of water and CO group from the $y_4$-ion is observed at 373.9 m/z. (C) Tandem mass spectrum of the 792.3 m/z ion from the peptide eluting first in the above chromatogram. The $b_{3-6}$-ions can be identified in the spectrum and all are shifted by 14 Da but the $y_3$ and $y_5$-ions are not shifted, suggesting that the modification lies on either the leucine or glutamic acid of the N-terminus. (D) Tandem mass spectrum of the 792.3 m/z ion from the peptide eluting second in the separation. The $b_5$ and $b_6$-ions contain the 14 Da shift as above, but the $b_3$ and $b_4$ ions do not, consistent with the methyl ester on the glutamic acid at position 5 in the peptide.

The identification of methyl esters on csPCNA with respect to the pI of the isoform was further investigated. PCNA has a calculated pI of approximately 4.5 and the pI of csPCNA, as determined after calibration of the 2D-PAGE gel using the pIs of surrounding proteins, was slightly higher, approximately 4.6. In contrast, if 100% of all 16 acidic residues identified in FIG. 2 were methyl esterified, the protein's pI would likely shift basic more dramatically than 0.1 pH units (e.g., 5.66). There may be additional residues that are modified to produce the basic or nmPCNA isoform. The nmPCNA isoform may also be methyl esterified on different and/or additional residues than csPCNA. The methods discloses herein enable one of ordinary skill in the art to determine methylesterification levels of csPCNA and nmPCNA. The relative abundances of the methyl esterified peptides was measured and compared to the unmodified peptides. This was accomplished by measuring and comparing the peak areas of each unmodified peptide and its methyl esterified counterpart. Comparison of the peak areas revealed a relative abundance for each methyl ester identified in this LC-MS/MS experiment as shown in Table II. Each of the peptides show only partial methyl esterification (<25%) when the peak areas are compared. Therefore the csPCNA isoform is likely to be comprised of a heterogeneous population of PCNA molecules with the same pI. In other words, a single csPCNA molecule likely exhibits one or few methyl esters, but not 16. But the one or few methyl esters can occur on 16 different residues throughout the protein. This heterogeneity of csPCNA is illustrated by the presence of methyl esterification on the C-terminal peptide of csPCNA. The unmodified peptide, IEDEEGS (778 m/z), eluted at 28.9 min (FIG. 3A) and the CID spectrum of this peptide is consistent with a peptide containing unmodified acidic residues (FIG. 3B). Interestingly, in the selected ion chromatogram for methyl esterified species (792 m/z) of this peptide, two peaks are identified with 2-3 min increased retention times. This is likely due to an increased hydrophobic character and loss of charge imparted by methyl esterification. The resolution of these two peaks was therefore indicative of a difference in structure of these peptides. Inspection of the CID spectra identifies that the peptides are methyl esterified but on different residues (FIGS. 3C and D). Because no peptides harboring methyl esters on both residues were observed, the appearance of these peptides most likely resulted from the analysis of a heterogeneous population of csPCNA.

It is possible that the observed heterogeneity and low percentage of modified species could be the result of the facile lability of the methyl ester modifications themselves. Some reports indicate that protein methyl esterification modifications were short lived in neutral and basic solutions. Therefore, protein methyl esters, like those found on csPCNA, can spontaneously hydrolyze leaving an unmodified residue and methanol. Additionally, the basic and oxidizing conditions of SDS-PAGE can also lead to loss of methyl esters from PCNA, and attempts to resolve the basic PCNA isoform, a highly methyl esterified form of PCNA, to its basic pI appears to display a spontaneous regression towards a more acidic pI (FIG. 4).

Figure 4:
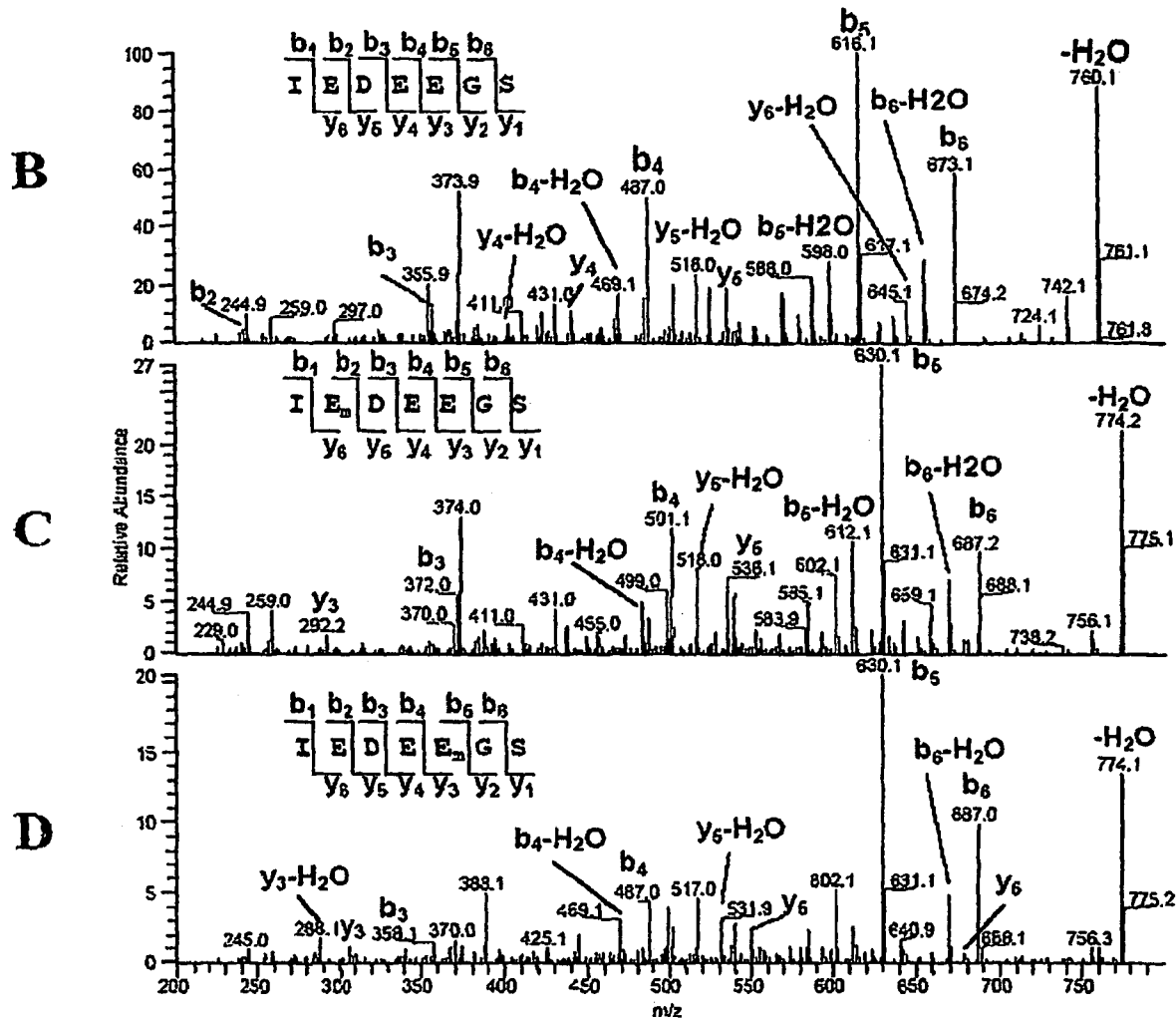
FIG. 4 shows immunoblot of PCNA.
Figure 4:
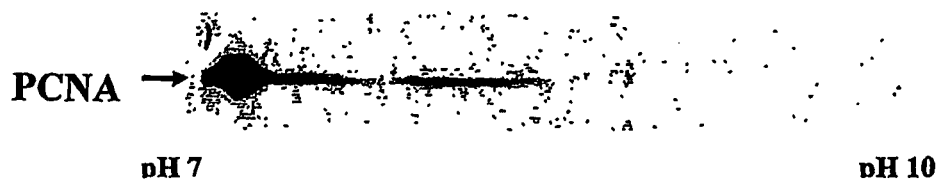

A high level of methyl esters likely cause PCNA to focus to a basic pI as shown in the immunoblot in FIG. 4 (approximately pH 8.8-9.0). However, focusing of this isoform may not be uniform (streaky) and may be present at a lower intensity. The basic pHs at which this isoform resolves may not be conducive to maintain all of the methyl esterification on the protein. The inability to focus at a specific pI observed on this gel (FIG. 4) is likely due to the concomitant loss of one or more of the methyl esters due to the focusing at a basic pH. Spontaneous hydrolysis of the methyl esters occur, liberating methanol and an unmodified amino acid side chain. Regeneration of the acidic side chains by this "basic hydrolysis" likely causes PCNA's pI to shift from a basic one to a more acidic one, as evidenced by the accumulation of PCNA towards the mores acidic side of the gel (pH 7).

Identification and analysis of methylesterification can be performed under conditions that minimize loss of methylesters. For example, a method describing acidic 2D-PAGE that uses conditions able to preserve protein methyl esters has been described (O'Connor et al., Anal Biochem 1985, 148, 79-86). However, many of the available proteases that recognize PCNA are active in neutral to basic pHs and it is possible that some significant amount of methyl esterification would be lost during the digestion.

In the intact cell or in extracts, the enzyme(s) responsible for the methyl esterification may be active and can modify residues that have lost methyl esters to spontaneous hydrolysis. Separation of PCNA from the enzyme(s) responsible for the methyl esterification and incubation in conditions supporting hydrolysis (e.g., pH above 7.0) may lead to loss of one or more methyl esters. For example, such loss of methyl esters can be minimized by maintaining a slightly acidic condition during sample handling and analysis.

TABLE I

Analysis of methylesterification status of various proteins.

| Spot[a] | Protein | Swissprot Accession | Molecular weight ($M_r$) | pI | Peptides Identified | Methyl Esterified Peptides[b] | Sequence coverage[c] |
|---|---|---|---|---|---|---|---|
| i | Ezrin | P15311 | 69,225 | 5.95 | 16 | 0 | 32% |
| ii | Stathmin | P16949 | 17,161 | 5.77 | 16 | 7 | 62% |
| iii | Calreticulin precursor | P27797 | 48,112 | 4.29 | 7 | 0 | 33% |

TABLE I-continued

Analysis of methylesterification status of various proteins.

| Spot[a] | Protein | Swissprot Accession | Molecular weight ($M_r$) | pI | Peptides Identified | Methyl Esterified Peptides[b] | Sequence coverage[c] |
|---|---|---|---|---|---|---|---|
| iv | Inorganic pyrophosphatase | Q15181 | 32,639 | 5.54 | 20 | 0 | 75% |
| v | Translationally controlled tumor protein | P13693 | 19583 | 4.84 | 8 | 0 | 70% |

[a]The locations of the protein spots are identified in FIG. 1A.
[b]Peptides clearly demonstrating +14 mass shift on either aspartic or glutamic acid residues.
[c]Sequence coverage is calculated by dividing the number of amino acid residues identified by the total number of residues in the protein.

TABLE II

Methylesterification state of various csPCNA-derived peptides.

| Peptide Sequence[a] | Observed m/z | Charge State | Calc. mass | Peak Area | Methyl Ester (%)[b] | Score[c] |
|---|---|---|---|---|---|---|
| $M_o FE_m AR$ | 343.37 | 2 | 682.31 | $5.9 \times 10^6$ | 3.6 | 19 |
| $IE_m DEEGS$ | 792.30 | 1 | 791.32 | $2.8 \times 10^7$ | 7.3 | 27 |
| $IEDEE_m GS$ | 792.47 | 1 | 791.32 | $2.7 \times 10^7$ | 7.0 | 25 |
| $VSDYE_m M_o K$ | 451.9 | 2 | 900.39 | $8.1 \times 10^6$ | 11.4 | 46 |
| $M_o PSGE_m FAR$ | 463.20 | 2 | 923.42 | $1.4 \times 10^7$ | 2.5 | 50 |
| $LSQTSNVD_m K$ | 503.96 | 2 | 1004.51 | $1.5 \times 10^6$ | 21.1 | 40 |
| $C_{ca} AGNE_m DIITLR$ | 639.44 | 2 | 1274.63 | $1.7 \times 10^7$ | 8.8 | 66 |
| $FSASGE_m LGNGNIK$ | 655.11 | 2 | 1306.65 | $7.6 \times 10^7$ | 2.7 | 99 |
| $AEDNADTLALVFEAPNQE_m K$ | 1045.93 | 2 | 2088.00 | $5.0 \times 10^7$ | 3.5 | 97 |
| $AE_m DNADTLALVFEAPNQEK$ | 1046.01 | 2 | 2088.00 | $2.0 \times 10^7$ | 3.9 | 89 |
| $AED_m NADTLALVFEAPNQEK$ | 1045.31 | 2 | 2088.00 | $4.1 \times 10^7$ | 12.7 | 102 |
| $AEDNADTLALVFE_m APNQEK$ | 1045.69 | 2 | 2088.00 | $3.4 \times 10^7$ | 4.5 | 94 |
| $LM_o D_m LDVEQLGIPEQEYSC_{ca} VVK$ | 1249.50 | 2 | 2494.20 | $9.5 \times 10^7$ | 10.3 | 78 |
| $ATPLSSTVTLSM_o SADVPLVVE_m YK$ | 1220.83 | 2 | 2437.27 | $1.35 \times 10^7$ | 8.3 | 95 |
| $LSQTSNVDKEEEAVTIEM_o NE_m PVQLTFALR$ | 1108.28 | 3 | 3320.64 | $3.43 \times 10^{9d}$ | 8.7 | 50 |

[a]Peptide modifications presented are oxidized methionine ($M_o$), carbamidomethyl cysteine ($C_{ca}$), methyl esterified glutamic acid ($E_m$), and methyl esterified aspartic acid ($D_m$).
[b]Percent methyl ester was calculated by dividing the peak areas of the methyl esterified peptides by the combined peak areas for the methyl esterified and unmodified peptides.
[c]Mascot scores are reported as $-10 \log(P)$, where P is the probability that the match is a random event.
[d]Data generated using an LCQ DECA XP compared to an LCQ Advantage.

TABLE III

Amino acid positions of methylesters on csPCNA

| Methyl Ester | Residue | Position (1-261 a.a.) |
|---|---|---|
| 1 | Glutamic acid | 3 |
| 2 | Glutamic acid | 85 |
| 3 | Glutamic acid | 93 |
| 4 | Aspartic acid | 94 |
| 5 | Glutamic acid | 104 |
| 6 | Glutamic acid | 109 |
| 7 | Glutamic acid | 115 |
| 8 | Aspartic acid | 120 |
| 9 | Glutamic acid | 132 |
| 10 | Glutamic acid | 143 |
| 11 | Glutamic acid | 174 |
| 12 | Aspartic acid | 189 |
| 13 | Glutamic acid | 201 |
| 14 | Glutamic acid | 238 |
| 15 | Glutamic acid | 256 |
| 16 | Glutamic acid | 259 |

We claim:

1. A method of detecting a cancer specific proliferating cell nuclear antigen (csPCNA) isoform in a biological sample, the method comprising: detecting a posttranslational modification comprising a methyl ester on one or more of 16 aspartic acid or glutamic acid residues corresponding to the amino acid positions 3, 85, 93, 94, 104, 109, 115, 120, 132, 143, 174, 189, 201, 238, 256, and 259 of SEQ ID NO: 30 in the sample suspected of containing the csPCNA isoform; and
comparing the levels of methyl esters on the csPCNA isoform with a nonmalignant isoform of PCNA, wherein the csPCNA isoform has a lower level of methyl esterification than the nonmalignant isoform of PCNA.

2. The method of claim 1, wherein the biological sample is a bodily fluid.

3. The method of claim 2, wherein the bodily fluid is selected from blood, plasma, lymph, serum, pleural fluid, spinal fluid, saliva, sputum, urine, gastric juice, pancreatic juice, ascites fluid, synovial fluid, milk, and semen.

4. The method of claim 1, wherein the biological sample is a tissue sample.

5. The method of claim 4, wherein the tissue is selected from breast, prostrate, lung, colon, epithelial, connective, cervical, esophageal, brain, thymus, thyroid, pancreas, testis, ovary, intestine, bladder, stomach, soft tissue sarcomas, osteosarcoma, leukemia, lymphoma, carcinoma, adenocarcinoma, placenta, fibrous, germ cell tissue, and extracts thereof.

6. The method of claim 1, wherein the methyl ester present on one or more of the 16 aspartic acid or glutamic acid residues corresponds to the peptides with modified amino acid residues selected from MFE$_m$AR (SEQ ID NO: 1);
IE$_m$DEEGS (SEQ ID NO: 2);
IEDEE$_m$GS (SEQ ID NO: 3);
VSDYE$_m$MK (SEQ ID NO: 4);
MPSGE$_m$FAR (SEQ ID NO: 5);
LSQTSNVD$_m$K (SEQ ID NO: 6);
CAGNE$_m$DIITLR (SEQ ID NO: 7);
FSASGE$_m$LGNGNIK (SEQ ID NO: 8);
AEDNADTLALVFEAPNQE$_m$K (SEQ ID NO: 9);
AE$_m$DNADTLALVFEAPNQEK (SEQ ID NO: 10);
AED$_m$NADTLALVFEAPNQEK (SEQ ID NO: 11);
AEDNADTLALVFE$_m$APNQEK (SEQ ID NO: 12);
LMD$_m$LDVEQLGIPEQEYSCVVK (SEQ ID NO: 13);
ATPLSSTVTLSMSADVPLVVE$_m$YK (SEQ ID NO: 14);
LSQTSNVDKEEEAVTIEMNE$_m$PVQLTFALR (SEQ ID NO: 15); and
LMDLDVEQLGIPEQE$_m$YSCVVK (SEQ ID NO: 31),
wherein E$_m$ represents a methylesterified glutamic acid residue and D$_m$ represents a methylesterified aspartic acid residue.

7. The method of claim 1, wherein the detection of csPCNA isoform is performed using a mass spectrometric analysis.

8. The method of claim 7, wherein the mass spectrometric analysis is liquid chromatography (LC) mass spectrometric (MS) analysis.

9. The method of claim 7, wherein the mass spectrometric analysis of a csPCNA-derived peptide results in a 14 Da mass shift as compared to a corresponding unmodified peptide.

* * * * *

```
                    SEQUENCE LISTING

<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: methylesterified Glu

<400> SEQUENCE: 1

Met Phe Glu Ala Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: methylesterified Glu

<400> SEQUENCE: 2

Ile Glu Asp Glu Glu Gly Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: methylesterified Glu

<400> SEQUENCE: 3

Ile Glu Asp Glu Glu Gly Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: methylesterified Glu

<400> SEQUENCE: 4

Val Ser Asp Tyr Glu Met Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: methylesterified Glu

<400> SEQUENCE: 5
```

```
Met Pro Ser Gly Glu Phe Ala Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: methylesterified Asp

<400> SEQUENCE: 6

Leu Ser Gln Thr Ser Asn Val Asp Lys
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: methylesterified Glu

<400> SEQUENCE: 7

Cys Ala Gly Asn Glu Asp Ile Ile Thr Leu Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: methylesterified Glu

<400> SEQUENCE: 8

Phe Ser Ala Ser Gly Glu Leu Gly Asn Gly Asn Ile Lys
1               5                   10

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)
<223> OTHER INFORMATION: methylesterified Glu

<400> SEQUENCE: 9

Ala Glu Asp Asn Ala Asp Thr Leu Ala Leu Val Phe Glu Ala Pro Asn
1               5                   10                  15

Gln Glu Lys

<210> SEQ ID NO 10
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: methylesterified Glu

<400> SEQUENCE: 10

Ala Glu Asp Asn Ala Asp Thr Leu Ala Leu Val Phe Glu Ala Pro Asn
 1               5                  10                  15

Gln Glu Lys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: methylesterified Asp

<400> SEQUENCE: 11

Ala Glu Asp Asn Ala Asp Thr Leu Ala Leu Val Phe Glu Ala Pro Asn
 1               5                  10                  15

Gln Glu Lys

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: methylesterified Glu

<400> SEQUENCE: 12

Ala Glu Asp Asn Ala Asp Thr Leu Ala Leu Val Phe Glu Ala Pro Asn
 1               5                  10                  15

Gln Glu Lys

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: methylesterified Asp

<400> SEQUENCE: 13

Leu Met Asp Leu Asp Val Glu Gln Leu Gly Ile Pro Glu Gln Glu Tyr
 1               5                  10                  15

Ser Cys Val Val Lys
            20
```

```
<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)
<223> OTHER INFORMATION: methylesterified Glu

<400> SEQUENCE: 14

Ala Thr Pro Leu Ser Ser Thr Val Thr Leu Ser Met Ser Ala Asp Val
 1               5                  10                  15

Pro Leu Val Val Glu Tyr Lys
            20

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)
<223> OTHER INFORMATION: methylesterified Glu

<400> SEQUENCE: 15

Leu Ser Gln Thr Ser Asn Val Asp Lys Glu Glu Glu Ala Val Thr Ile
 1               5                  10                  15

Glu Met Asn Glu Pro Val Gln Leu Thr Phe Ala Leu Arg
            20                  25

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Glu Asp Glu Glu Gly Ser
 1               5

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Glu Asp Asn Ala Asp Thr Leu Ala Leu Val Phe Glu Ala Pro Asn
 1               5                  10                  15

Gln Glu Lys

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 18

Asp Leu Ile Asn Glu Ala Cys Trp Asp Ile Ser Ser Ser Gly Val Asn
1               5                   10                  15

Leu Gln Ser Met Asp Ser Ser His Val Ser Leu Val Gln Leu Thr Leu
            20                  25                  30

Arg

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: oxidized Met
<220> FEATURE:
<221> NAME/KEY: MOD_RES
<222> LOCATION: (3)
<223> OTHER INFORMATION: methylesterified Glu

<400> SEQUENCE: 19

Met Phe Glu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: methylesterified Glu
<220> FEATURE:
<221> NAME/KEY: MOD_RES
<222> LOCATION: (6)
<223> OTHER INFORMATION: oxidized Met

<400> SEQUENCE: 20

Val Ser Asp Tyr Glu Met Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: oxidized Met
<220> FEATURE:
<221> NAME/KEY: MOD_RES
<222> LOCATION: (5)
<223> OTHER INFORMATION: methylesterified Glu

<400> SEQUENCE: 21

Met Pro Ser Gly Glu Phe Ala Arg
1               5

<210> SEQ ID NO 22
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: carbamidomethyl Cys
<220> FEATURE:
<221> NAME/KEY: MOD_RES
<222> LOCATION: (5)
<223> OTHER INFORMATION: methylesterified Glu

<400> SEQUENCE: 22

Cys Ala Gly Asn Glu Asp Ile Ile Thr Leu Arg
1               5                   10

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: oxidized Met
<220> FEATURE:
<221> NAME/KEY: MOD_RES
<222> LOCATION: (3)
<223> OTHER INFORMATION: methylesterified Asp
<220> FEATURE:
<221> NAME/KEY: MOD_RES
<222> LOCATION: (18)
<223> OTHER INFORMATION: carbamidomethyl Cys

<400> SEQUENCE: 23

Leu Met Asp Leu Asp Val Glu Gln Leu Gly Ile Pro Glu Gln Glu Tyr
1               5                   10                  15

Ser Cys Val Val Lys
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: oxidized Met
<220> FEATURE:
<221> NAME/KEY: MOD_RES
<222> LOCATION: (21)
<223> OTHER INFORMATION: methylesterified Glu

<400> SEQUENCE: 24

Ala Thr Pro Leu Ser Ser Thr Val Thr Leu Ser Met Ser Ala Asp Val
1               5                   10                  15

Pro Leu Val Val Glu Tyr Lys
            20

<210> SEQ ID NO 25
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (18)
<223> OTHER INFORMATION: oxidized Met
<220> FEATURE:
<221> NAME/KEY: MOD_RES
<222> LOCATION: (20)
<223> OTHER INFORMATION: methylesterified Glu

<400> SEQUENCE: 25

Leu Ser Gln Thr Ser Asn Val Asp Lys Glu Glu Glu Ala Val Thr Ile
 1               5                  10                  15

Glu Met Asn Glu Pro Val Gln Leu Thr Phe Ala Leu Arg
            20                  25

<210> SEQ ID NO 26
<211> LENGTH: 261
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: methylesterified Glu
<220> FEATURE:
<221> NAME/KEY: MOD_RES
<222> LOCATION: (85)
<223> OTHER INFORMATION: methylesterified Glu
<220> FEATURE:
<221> NAME/KEY: MOD_RES
<222> LOCATION: (93)
<223> OTHER INFORMATION: methylesterified Glu
<220> FEATURE:
<221> NAME/KEY: MOD_RES
<222> LOCATION: (94)
<223> OTHER INFORMATION: methylesterified Asp
<220> FEATURE:
<221> NAME/KEY: MOD_RES
<222> LOCATION: (104)
<223> OTHER INFORMATION: methylesterified Glu
<220> FEATURE:
<221> NAME/KEY: MOD_RES
<222> LOCATION: (109)
<223> OTHER INFORMATION: methylesterified Glu
<220> FEATURE:
<221> NAME/KEY: MOD_RES
<222> LOCATION: (115)
<223> OTHER INFORMATION: methylesterified Glu
<220> FEATURE:
<221> NAME/KEY: MOD_RES
<222> LOCATION: (120)
<223> OTHER INFORMATION: methylesterified Asp
<220> FEATURE:
<221> NAME/KEY: MOD_RES
<222> LOCATION: (143)
<223> OTHER INFORMATION: methylesterified Glu
<220> FEATURE:
<221> NAME/KEY: MOD_RES
<222> LOCATION: (174)
<223> OTHER INFORMATION: methylesterified Glu
<220> FEATURE:
<221> NAME/KEY: MOD_RES
<222> LOCATION: (189)
<223> OTHER INFORMATION: methylesterified Asp
<220> FEATURE:
<221> NAME/KEY: MOD_RES
<222> LOCATION: (201)
<223> OTHER INFORMATION: methylesterified Glu
<220> FEATURE:
<221> NAME/KEY: MOD_RES
<222> LOCATION: (238)
<223> OTHER INFORMATION: methylesterified Glu
<220> FEATURE:
<221> NAME/KEY: MOD_RES
<222> LOCATION: (256)
```

<223> OTHER INFORMATION: methylesterified Glu
<220> FEATURE:
<221> NAME/KEY: MOD_RES
<222> LOCATION: (259)
<223> OTHER INFORMATION: methylesterified Glu

<400> SEQUENCE: 26

```
Met Phe Glu Ala Arg Leu Val Gln Gly Ser Ile Leu Lys Lys Val Leu
  1               5                  10                  15
Glu Ala Leu Lys Asp Leu Ile Asn Glu Ala Cys Trp Asp Ile Ser Ser
             20                  25                  30
Ser Gly Val Asn Leu Gln Ser Met Asp Ser Ser His Val Ser Leu Val
         35                  40                  45
Gln Leu Thr Leu Arg Ser Glu Gly Phe Asp Thr Tyr Arg Cys Asp Arg
 50                  55                  60
Asn Leu Ala Met Gly Val Asn Leu Thr Ser Met Ser Lys Ile Leu Lys
 65                  70                  75                  80
Cys Ala Gly Asn Glu Asp Ile Ile Thr Leu Arg Ala Glu Asp Asn Ala
                 85                  90                  95
Asp Thr Leu Ala Leu Val Phe Glu Ala Pro Asn Gln Glu Lys Val Ser
            100                 105                 110
Asp Tyr Glu Met Lys Leu Met Asp Leu Asp Val Glu Gln Leu Gly Ile
        115                 120                 125
Pro Glu Gln Glu Tyr Ser Cys Val Val Lys Met Pro Ser Gly Glu Phe
130                 135                 140
Ala Arg Ile Cys Arg Asp Leu Ser His Ile Gly Asp Ala Val Val Ile
145                 150                 155                 160
Ser Cys Ala Lys Asp Gly Val Lys Phe Ser Ala Ser Gly Glu Leu Gly
                165                 170                 175
Asn Gly Asn Ile Lys Leu Ser Gln Thr Ser Asn Val Asp Lys Glu Glu
            180                 185                 190
Glu Ala Val Thr Ile Glu Met Asn Glu Pro Val Gln Leu Thr Phe Ala
        195                 200                 205
Leu Arg Tyr Leu Asn Phe Phe Thr Lys Ala Thr Pro Leu Ser Ser Thr
210                 215                 220
Val Thr Leu Ser Met Ser Ala Asp Val Pro Leu Val Val Glu Tyr Lys
225                 230                 235                 240
Ile Ala Asp Met Gly His Leu Lys Tyr Tyr Leu Ala Pro Lys Ile Glu
                245                 250                 255
Asp Glu Glu Gly Ser
            260
```

<210> SEQ ID NO 27
<211> LENGTH: 261
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: methylesterified Glu
<220> FEATURE:
<221> NAME/KEY: MOD_RES
<222> LOCATION: (85)
<223> OTHER INFORMATION: methylesterified Glu
<220> FEATURE:
<221> NAME/KEY: MOD_RES
<222> LOCATION: (104)
<223> OTHER INFORMATION: methylesterified Glu
<220> FEATURE:

```
<221> NAME/KEY: MOD_RES
<222> LOCATION: (109)
<223> OTHER INFORMATION: methylesterified Glu
<220> FEATURE:
<221> NAME/KEY: MOD_RES
<222> LOCATION: (115)
<223> OTHER INFORMATION: methylesterified Glu
<220> FEATURE:
<221> NAME/KEY: MOD_RES
<222> LOCATION: (143)
<223> OTHER INFORMATION: methylesterified Glu
<220> FEATURE:
<221> NAME/KEY: MOD_RES
<222> LOCATION: (174)
<223> OTHER INFORMATION: methylesterified Glu
<220> FEATURE:
<221> NAME/KEY: MOD_RES
<222> LOCATION: (256)
<223> OTHER INFORMATION: methylesterified Glu

<400> SEQUENCE: 27

Met Phe Glu Ala Arg Leu Val Gln Gly Ser Ile Leu Lys Lys Val Leu
 1               5                  10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser His Val Ser Leu Val
        35                  40                  45

Gln Leu Thr Leu Arg Ser Glu Gly Phe Asp Thr Tyr Arg Cys Asp Arg
 50                  55                  60

Asn Leu Ala Met Gly Val Asn Leu Thr Ser Met Ser Lys Ile Leu Lys
 65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260

<210> SEQ ID NO 28
<211> LENGTH: 141
<212> TYPE: PRT
<213> ORGANISM: Artificial Sequence
<220> FEATURE:
<223> OTHER INFORMATION: Description of Artificial Sequence: Synthetic
```

```
                       peptide
<220> FEATURE:
<221> NAME/KEY: MOD_RES
<222> LOCATION: (43)
<223> OTHER INFORMATION: methylesterified Glu
<220> FEATURE:
<221> NAME/KEY: MOD_RES
<222> LOCATION: (54)
<223> OTHER INFORMATION: methylesterified Asp
<220> FEATURE:
<221> NAME/KEY: MOD_RES
<222> LOCATION: (66)
<223> OTHER INFORMATION: methylesterified Glu

<400> SEQUENCE: 28

Ala Leu Lys Asp Leu Ile Asn Glu Ala Cys Trp Asp Ile Ser Ser Ser
 1               5                  10                  15

Gly Val Asn Leu Gln Ser Met Asp Ser Ser His Val Ser Leu Val Gln
             20                  25                  30

Leu Thr Leu Arg Ser Glu Ala Pro Asn Gln Glu Lys Val Ser Asp Tyr
         35                  40                  45

Glu Met Lys Leu Met Asp Leu Asp Val Glu Gln Leu Gly Ile Pro Glu
     50                  55                  60

Gln Glu Tyr Ser Cys Val Val Lys Met Pro Ser Gly Glu Leu Gly Asn
 65                  70                  75                  80

Gly Asn Ile Lys Leu Ser Gln Thr Ser Asn Val Asp Lys Glu Glu Glu
                 85                  90                  95

Ala Val Thr Ile Glu Met Asn Glu Pro Val Gln Leu Thr Phe Ala Leu
            100                 105                 110

Arg Tyr Leu Asn Phe Phe Thr Lys Ala Thr Pro Leu Ser Ser Thr Val
        115                 120                 125

Thr Leu Ser Met Ser Ala Asp Val Pro Leu Val Val Glu
    130                 135                 140

<210> SEQ ID NO 29
<211> LENGTH: 154
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Leu Ile Asn Glu Ala Cys Trp Asp Ile Ser Ser Ser Gly Val Asn
 1               5                  10                  15

Leu Gln Ser Met Asp Ser Ser His Val Ser Leu Val Gln Leu Thr Leu
             20                  25                  30

Arg Ser Glu Gly Phe Asp Arg Asn Leu Ala Met Gly Val Asn Leu Thr
         35                  40                  45

Ser Met Ser Lys Ile Leu Lys Cys Ala Gly Asn Glu Asp Ile Ile Thr
     50                  55                  60

Leu Arg Ala Glu Asp Asn Ala Asp Thr Leu Ala Leu Val Phe Glu Ala
 65                  70                  75                  80

Pro Asn Gln Glu Lys Val Ser Asp Tyr Glu Met Lys Leu Met Asp Leu
                 85                  90                  95

Ser His Ile Gly Asp Gly Val Lys Phe Ser Ala Ser Gly Glu Leu Gly
            100                 105                 110

Asn Gly Asn Ile Lys Leu Ser Gln Thr Ser Asn Val Asp Val Pro Leu
        115                 120                 125

Val Val Glu Tyr Lys Ile Ala Asp Met Gly His Leu Lys Tyr Tyr Leu
    130                 135                 140
```

Ala Pro Lys Ile Glu Asp Glu Glu Gly Ser
145                 150

<210> SEQ ID NO 30
<211> LENGTH: 261
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence:  Synthetic
      peptide
<220> FEATURE:
<221> NAME/KEY: MOD_RES
<222> LOCATION: (15)
<223> OTHER INFORMATION: methylesterified GLU

<400> SEQUENCE: 31

```
Leu Met Asp Leu Asp Val Glu Gln Leu Gly Ile Pro Glu Gln Glu Tyr
1               5                   10                  15

Ser Cys Val Val Lys
                20
```